United States Patent [19]

Sanz et al.

[11] 3,999,868
[45] Dec. 28, 1976

[54] UNIT FOR USE IN OPTICAL ANALYSIS

[76] Inventors: Manuel Sanz, 50B, ch. des Verjus, 1212 Grand-Lancy, Geneva; Georges Revillet, 20, ch. Francois-Chavaz, 1213 Onex, Geneva, both of Switzerland

[22] Filed: Nov. 17, 1975

[21] Appl. No.: 632,568

[30] Foreign Application Priority Data

Nov. 29, 1974 Switzerland .................. 15858/74

[52] U.S. Cl. ........................... 356/246; 233/26; 250/576; 356/197
[51] Int. Cl.² ................... G01N 1/10; B04B 9/12
[58] Field of Search .......... 356/196, 197, 198, 246; 233/11, 26; 250/573, 576

[56] References Cited

UNITED STATES PATENTS 3,713,775   1/1973   Schmitz ............................ 356/197
3,844,662   10/1974  Froreich ........................... 356/197

Primary Examiner—Vincent P. McGraw
Attorney, Agent, or Firm—Wallenstein, Spangenberg, Hattis & Strampel

[57] ABSTRACT

A unit for use in optical analysis is adapted to be mounted in a radial position on a centrifuging rotor and comprises a straight tubular cell. One end of the tubular cell is open and the other end is closed by an optically transparent wall which is substantially perpendicular to the longitudinal axis of the cell. The cell receives one component of a solution to be optically analysed and a second component of the solution is received in a recess of a cover of the unit releasably secured in a position closing the open end of the cell. The cover is formed with an aperture connecting the recess of the cover to the cell in the closed position, so that the second component can flow into the cell during centrifuging.

5 Claims, 11 Drawing Figures

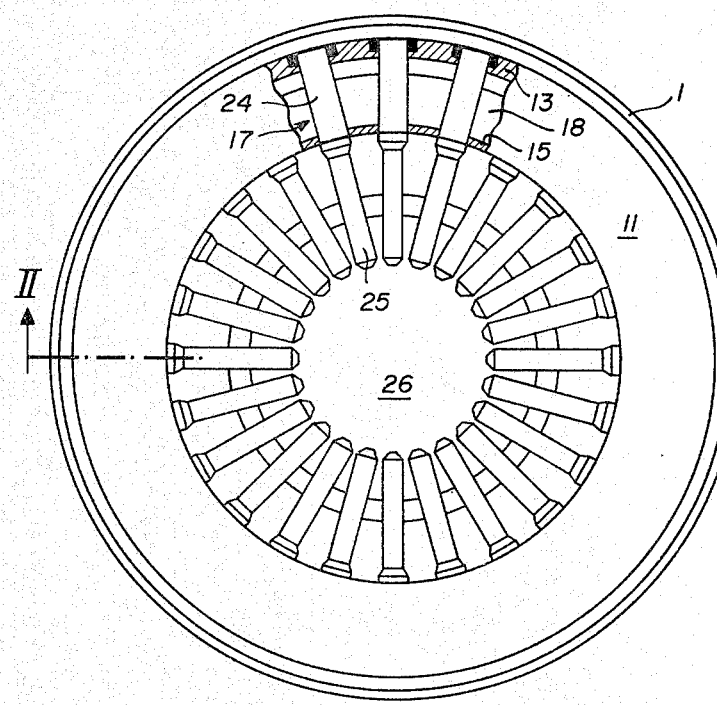
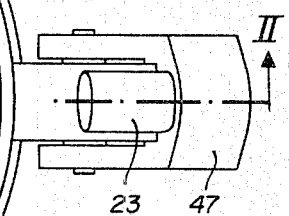
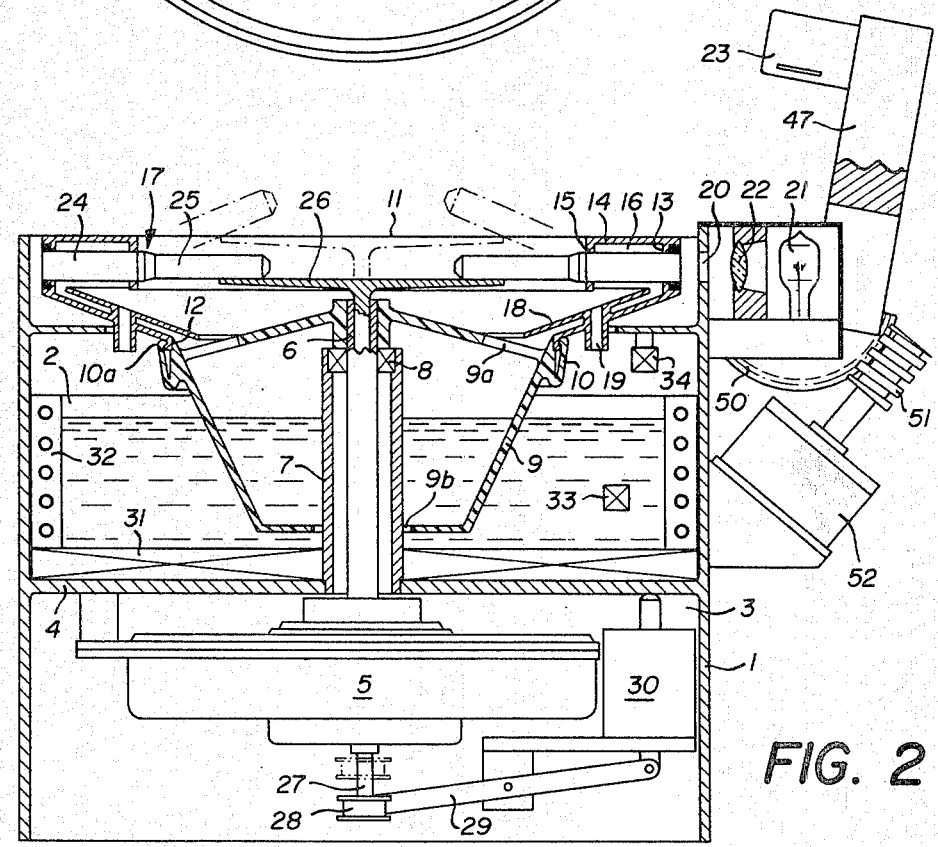
FIG. 1
FIG. 2

UNIT FOR USE IN OPTICAL ANALYSIS

BACKGROUND

This invention relates to a unit for containing a solution to be optically analyzed.

It has already been suggested that a number of small containers or receptacles be placed on a rotor and a solution in each receptacle be analyzed photometrically by means of a light beam which intersects the path described by the receptacles and by measuring the intensity of the light beam issuing from each receptacle.

A known analyser employing this suggestion comprises a rotor which is formed with a number of radial recesses each communicating with an analysis receptacle disposed at the outside end of the recess. Each such recess is divided into at least two compartments adapted to receive a product for analysis and at least one reagent, respectively. The centrifugal force arising from rotation of the rotor has the effect of displacing the liquid from the inner compartment towards the outer compartment and then of transferring the resulting mixture to the analysis receptacle.

The main disadvantage of such rotors is that they need cleaning after each analysis before being reused, so that the time wasted is considerable in respect of both cleaning and loading the apparatus with the reagents and samples.

In endeavours to obviate this disadvantage a rotor based on the same underlying idea but which is discarded after use and which is mounted releasably on a rotating support was studied. Such rotors are relatively costly, and so it is a costly business to use a new rotor for each new series of analyses.

Yet another disadvantage is the design of the analysis receptacle. The light beam passes through only some of the solution to be analyzed in all the receptacles, and so the number of molecules which are to be detected and which the light beam encounters depends upon the concentration of the mixture and upon the thickness of the layer of liquid through which the light beam passes. Consequently, the quantity of the sample, the quantity of the or each reagent and vessel dimensions are further factors affecting measurement accuracy.

SUMMARY

It is an object of the invention to increase the speed and flexibility of operation of such optical analyzers. It is another object of the invention to improve the accuracy of analysis by making analysis less dependent on measurement accuracy factors. It is another object of the invention to provide a solution of the problem which is more advantageous economically than the former solutions.

Accordingly, the present invention provides a unit for containing a solution to be optically analyzed and for mounting in a radial position on a centrifuging rotor, which unit comprises a straight tubular cell for containing a first component of the solution and having one end open and the other end closed by an optically transparent wall which is substantially perpendicular to the longitudinal axis of the cell, a cover and means releasably to secure the cover in a position closing the open end of the cell, the cover being formed with a recess for containing a second component of the solution and with at least one aperture connecting the said recess to the cell in the closed position, through which aperture the second component can flow into the cell during centrifuging.

BRIEF DESCRIPTION OF DRAWINGS

In order that the invention may be readily understood, an embodiment thereof will now be described, by way of example, with reference to the accompanying drawings, in which:

FIG. 1 is a plan view of an analyzer apparatus in which units embodying the invention are employed;

FIG. 2 is a sectional view on line II—II of FIG. 1;

DESCRIPTION OF PREFERRED EMBODIMENTS

Figure 3:
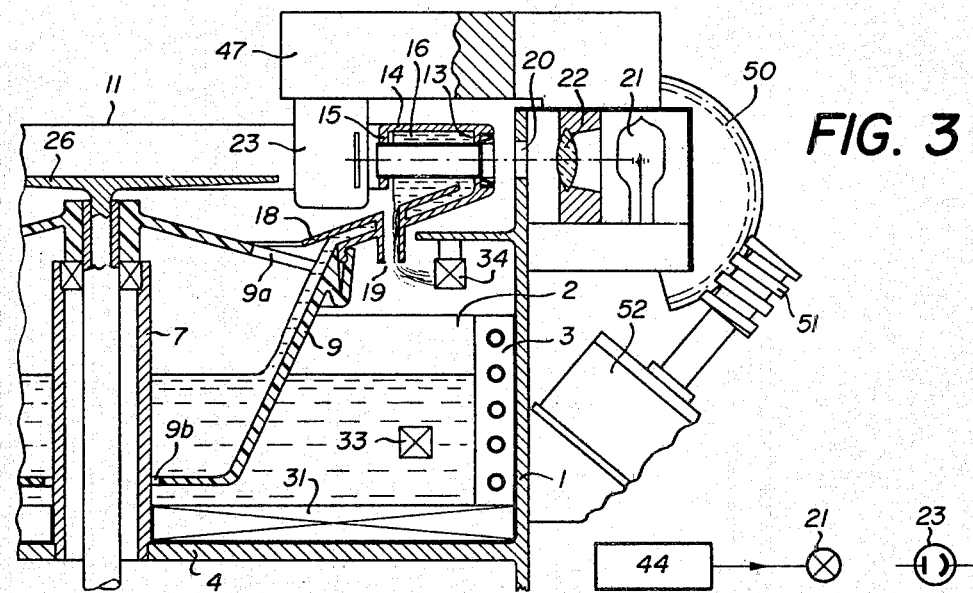
FIG. 3 is a view corresponding to part of FIG. 2 and showing the apparatus during the analysis phase.

The apparatus shown in FIGS. 1 to 3 comprises an outer casing 1 divided by a horizontal partition 4 into two chambers 2, 3 disposed one above the other. The top chamber 2 serves as a tank or vat for a purpose to be described hereinafter, and the bottom chamber 3 houses a d.c. driving motor 5 having a tubular shaft 6 extending through partition 4. Extending around shaft 6 is a sleeve 7 which is secured to partition 4 and which carries at its top end a bearing 8 for shaft 6. The top end of shaft 6 projects beyond sleeve 7 and is rigidly secured to a circular cage 9 which is coaxial with shaft 6 and which extends towards the bottom of the chamber 2. Cage 9 is trunco-conical in shape, with the apex of the cone directed downwardly. The top of the cage, which is connected to shaft 6, is formed with a number of orifices 9a and the base of the cage defines with the sleeve 7 an annular orifice 9b. The function of these orifices will be described hereinafter. Extending around the outer top edge of cage 9 are a number of resilient clamping members or grippers, comprising upwardly extending resilient arms 10 which exert a gripping force operative radially towards the axis of cage 9. Each arm 10 terminates in an internal enlargement 10a.

The resilient arms 10 releasably secure an analysis rotor 11 to the cage 9. The rotor 11 accordingly has a mounting collar 12 which can be seen in FIG. 4 and which is adapted to force aside the arms 10 and engage in the gripping members when a downwards axial pressure is applied to the rotor 11 after the same has been placed on top of the cage 9. The collar 12 also has an external bead adapted to engage below the enlargement 10a of each arm 10.

The rotor 11 flares away from the collar 12, the flared part terminating in a rising vertical annular partition 13 merging into a horizontal annular partition 14 which extends back towards the interior of the rotor and which merges into a second descending vertical annular partition 15, to bound an annular chamber 16. The two partitions 13, 15 are apertured, each aperture in one partition being centred on a radius common to one of the apertures in the other partition. Gaskets 46 extend around the orifices of the outer wall 13.

Each pair of apertures centred on a common radius is adapted to receive a tubular analysis unit 17 which is loaded, for optical analysis, with a solution. Such unit will be described in greater detail hereinafter.

An annular element 18 extends parallel to and above the flared part of rotor 11 and cooperates with the latter part to bound a passage between the cage orifices 9a and the annular chamber 16. Element 18 is secured to rotor 9 by way of vertical tubes 19 which extend through the flared part of the rotor.

Casing 1 is formed with a window 20 whose axis is coplanar with the path followed by the longitudinal axis of the tubular analysis units 17 on rotation of rotor 11. A light source, in the form of a bulb 21 and a lens 22, is mounted outside the casing 1 and is adapted to transmit a light beam along the axis of window 20. A light detector in the form of a photomultiplier 23 is secured to the end of an arm 47 pivoting in a vertical plane around an axis perpendicular to the axis of window 20. The arm 47 can be pivoted between two end positions, namely a lowered position, in which the cell of detector 23 is disposed on the axis of the beam from bulb 21, as shown in FIG. 3, and a raised position, in which the cell of detector 23 is in a position remote from the rotor 11, as shown in FIG. 2. Accordingly, arm 47 has a quadrant rack or the like 50 meshing with a worm 51 rigidly secured to the drive shaft of a motor 52.

Figure 7:
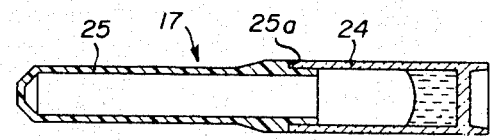

Each unit 17 comprises two parts, one of which is an analysis cell or enclosure 24 constituted by a cylindrical tube closed at one end by a flat end wall perpendicular to the longitudinal axis of the tube. The tube 24 is made of a transparent substance such as glass or a transparent plastics. Alternatively, only the end wall need be transparent and can be fitted to the tube. In all cases, the end wall is preferably recessed from the tube end. The second part of unit 17 is a cover 25 constituted by a second tube which is closed at one end and whose other end has a portion of an outer diameter corresponding to the inner diameter of the open end of the first tube (FIG. 7). Such portion, which is adapted to engage in the first tube 24, terminates in a bearing surface 25a which can be seen in FIG. 10 and which limits the extent to which cover 25 can enter unit 24. Cover 25 is made of a soft material which can be perforated by a hollow metal needle, such as an injection needle, for a purpose to be described hereinafter. Cover 25 need not be transparent. Unit 24 and cover 25 are of substantially the same volume as one another.

The analyzer shown in FIG. 2 also comprises a cover ejection mechanism, in the form of a disc 26 rigidly secured to a rod 27 received in the axial passage extending through shaft 6. Rod 27 projects below motor 5 and carries a grooved disc 28 visible in FIG. 2. One end of a lever 29 is engaged in the groove of disc 28, the other end of lever 29 being pivotally connected to the core of a solenoid 30. Between its two ends lever 29 is pivotally connected to a horizontal pivot pin rigidly secured to casing 1. When in its normal position, shown in solid lines in FIG. 2, disc 26 acts as a support for the covers 25 for a purpose to be described hereinafter; when in its ejection position, shown in chain-dotted lines, disc 26 disengages the covers 25 from the units 24.

There is a heater 31 at the bottom of tank 2 and the side wall thereof has a cooling circuit 32 connected e.g. to a source of cold water (not shown). Two temperature detectors 33,34 are disposed in the tank 2 and at the exit, respectively, of the rotor tubes 19.

Figure 5:
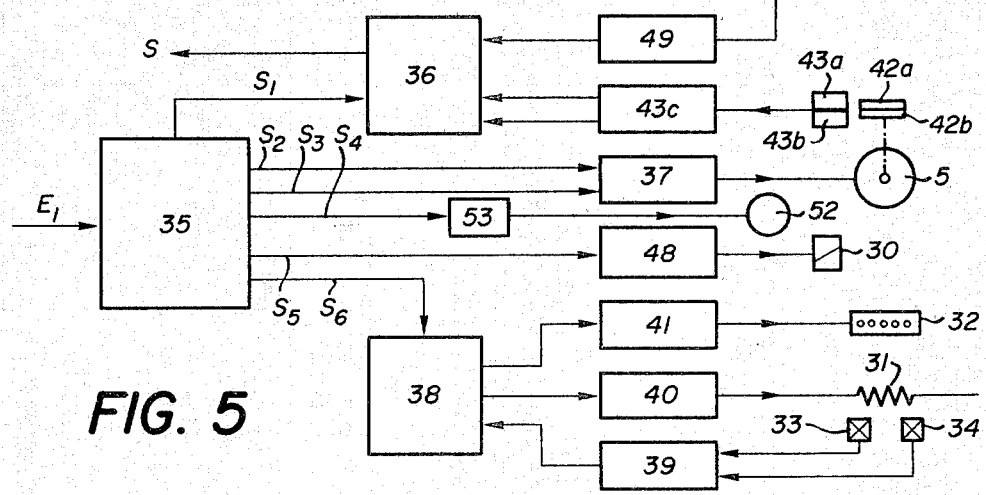
FIG. 5 is a block schematic diagram of a control circuit for the apparatus.

The system represented in the block schematic diagram of FIG. 5 provides supervision and control of the temperature of the bath in the tank 2 and the control of the various mechanisms of the complete apparatus.

Forming part of the system of FIG. 5 is an automatic sequence control device 35 for the analysis procedure, such device being connected by way of an input $E_1$ to a start button (not shown), the six outputs of the device serving to control the various mechanisms of the apparatus. One output $S_1$ is connected to the input of an information-acquiring element 36, outputs $S_2$ and $S_3$ are connected to a control amplifier 37 for motor 5, one output $S_2$ operator the amplifier 37 on d.c. and the other output $S_3$ operates the amplifier 37 on d.c., the output $S_5$ controls an amplifier 48 connected to solenoid 30, the output $S_4$ controls an amplifier 53 energizing motor 52, and output $S_6$ controls a supervisory element 38 for the temperature of the bath in tank 2. By way of an amplifier 39 the element 38 receives the average of the temperatures detected by the detectors 33, 34 and, depending upon the reference temperature set up at the output of the control 35, element 38 energizes either the heating amplifier 40 or the cooling amplifier 41, connected to the heater 31 and cooling circuit 32 respectively, so as to stabilize the average of the temperatures detected by the detectors 33 and 34 at a value substantially equal to the reference temperature of the control device 35.

Rotor shaft 6 which is also the output shaft of motor 5, is rigidly secured to two tracks 42a, 42b adapted to produce pulses in two photodetectors 43a, 43b respectively which are connected to the input of an amplifier 43c, the outputs thereof being connected to the information-obtaining element 36. The photodetectors 42a, 42b are adapted to deliver sync pulses to element 36. Accordingly, the first track 42a, which is associated with photodetector 43a, has one mark per unit 17 whereas the second track 42b, associated with photodetector 43b, has one mark for each revolution of the rotor 11, such mark serving to identify the first unit 17 and therefore the following units 17. Identification is by means of a counter which forms part of the element 36 and which is zero reset at each revolution by the track 42b and which then counts each pulse produced as each mark of track 42a passes by the photodetector 43a.

Bulb 21 is connected to a stabilized power supply 44, and photomultiplier 23 is connected to a high-voltage power supply 45. The input of an amplifier 49 of photomultiplier 23 is also connected thereto, the output of amplifier 49 being connected to the input of element 36. Because of the sync signals from photodetector 43a, only the data concerning the various samples are delivered at output S of element 36 whenever a sample passes by the photomultiplier 23, and each data item is identified with a specific sample through the agency of the second track 42b which indicates the passage of the first sample once per revolution of the rotor 11, as hereinbefore described.

Now that the apparatus has been described, a description will be given of the various phases occurring througout the analysis procedure, reference being made more particularly to FIGS. 6 – 11 which show the unit 17 during various phases of the procedure.

Figure 6:
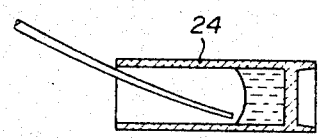
FIGS. 6 to 11 are sectional views of an analysis unit embodying the invention during various phases of the analysis procedure.

Referring to FIG. 6, reagent is placed at the bottom of the cell 24, by means of a pipette if the reagent is a liquid. Only the delivery end of the pipette is visible in FIG. 6, the pipette not forming part of this invention. Of course, solid reagents, e.g. in AFD form, can also be used, and so the units 17 can be prepared ready supplied with the or each required reagent. This step can be performed during the manufacture of the unit 17.

After the reagent has been introduced in one form or another, cover 25 is engaged in the aperture of enclosure 24 in the manner shown in FIG. 5.

Figure 8:
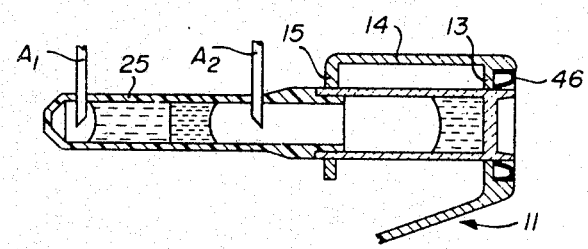

Rotor 11 is then loaded by the unit 17 being introduced from the outside and moved towards the rotor axis into the position shown in FIG. 8. Gasket 46 clamps cell 24 so that wall 13 of the annular chamber 16 is sealed.

Figure 4:
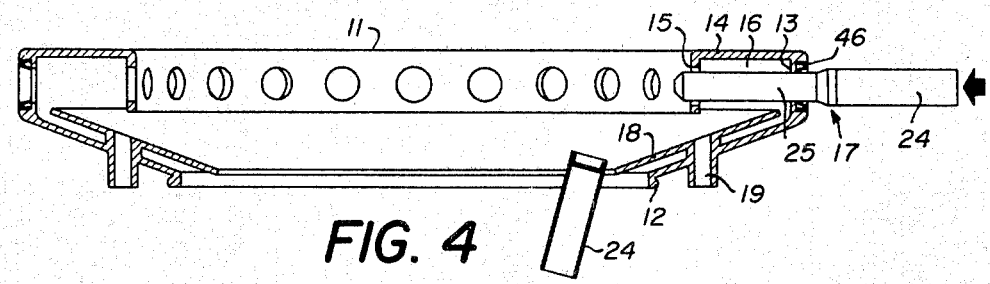
FIG. 4 shows the rotor separately from the apparatus during the charging or loading phase.

As can be seen in FIG. 4, the positioning of unit 17 ejects the previously used cell 24. As can also be gathered from FIG. 4, the units are placed on the rotor 11 preferably before the same is mounted on the cage 9 — a considerable advantage since a number of rotors can be prepared beforehand without any need to stop the analyzer.

Rotor 11 can then be secured to cage 9 for the loading of the samples. As FIG. 2 shows, once the rotor 11 has been mounted on cage 9 the covers 25 are supported by disc 26. As FIG. 8 shows, the cover 25 can then be pierced by two hollow needles $A_1$, $A_2$, the needle $A_1$ being the delivery end of a pipette (not shown) while needle $A_2$ is simply a vent. The liquid sample E which it is required to analyse, plus some water for dilution, are introduced through needle $A_1$. Introducing the sample via a needle which has penetrated the wall of cover 25 has the very considerable advantage of cleaning the outside of the needle tip, the inside of the needle being cleaned when the dilution water is introduced. The latter also ensures that all the sample has been introduced into the unit 17.

The inner diameter of cover 25 is such that the surface tension of the liquid introduced forms a meniscus which prevents the liquid from flowing into the analysis cell 24. It is found that all the sample and all the water are contained in cover 25, and this is the reason why the cover 25 is of substantially the same volume as the enclosure 24.

Figure 9:
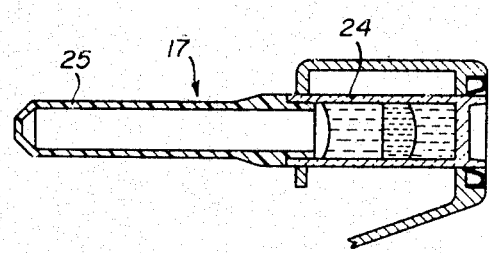
Figure 10:
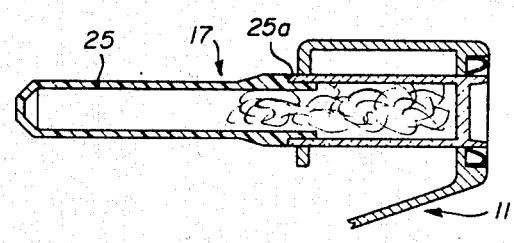
Figure 11:
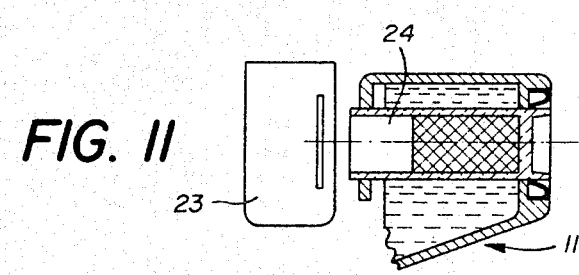

Once all the samples have been transferred into the respective analysis units 17, a brief centrifuging transfers the liquids into the cells 24 where they contact the liquid or AFD reagents (FIG. 9), whereafter the solution is mixed and homogenized. To this end, the automatic sequence control device 35 shown in FIG. 5 delivers a signal at its output $S_3$ for the amplifier 37 to energize motor 5 on a.c. Since motor 5 is a d.c. motor, when it is energized on a.c. it oscillates the shaft 6 at the same frequency as the a.c. used to energize motor 5. The oscillating motion of rotor 11 causes intense agitation of the liquids or of the liquids and solid reagent in the units 17, as shown in FIG. 10, the agitation mixing the liquids and/or dissolving the solid reagent in the liquid.

Motor 5 is then energized on d.c. to centrifuge the solution, motor 5 rotating the rotor at a speed of approximately 1000 r.p.m. The purpose of such centrifuging is to degas the solution by expelling bubbles which are lighter than the liquid. The bubbles are the result of the liquid being agitated. Another effect of the centrifuging is that all the solution is transferred to the analysis cell 24. The covers 25 are then ejected by operation of solenoid 30 which acts by way of lever 29 to raise the disc 26.

Cell 24 is ready for optical analysis of the solution in it. To this end, a controlled-temperature water-circulation circuit is provided which can bring the solution to an appropriate temperature during the measurement process. Water is introduced into tank 2 and, through the annular orifice 9b visible in FIGS. 2 and 3, enters cage 9. The water therein experiences centrifugal force as cage 9 rotates and, because of the trunco-conical shape of cage 9, a layer of water forms on the inside trunco-conical surface of cage 9, is hurled through the orifices 9a and reaches the rotor passage bounded by the flared part of the rotor and the annular element 18 and enters the annular chamber 16 through which the cells 24 pass. The excess of water arriving continuously in chamber 16 returns through the discharge or drain tubes 19 to tank 2. Because of the centrifugal force which produces the flow through the water-circulation circuit, the water leaving the tube 19 is hurled outwards. Consequently, the detector 34 which is disposed below and inside the exit end of the tubes 19, receives the stream of water issuing therefrom and can measure the temperature of such water. The circuit has other uses, as in centrifuges or any other use where a rotor is involved.

For optical analysis of the solutions in each cell 24, the control device 35 transmits a signal to amplifier 53 which starts motor 52, the same driving worm 51 to lower the arm 47 carrying photomultiplier 23 into the position shown in FIG. 3. Each mark on the first track of the photodetector 42a causes a data item to be delivered at output S of element 36. The width and the position of the respective marks on the first track of photodetector 42a are such that the data item output corresponds to the instant of time when the longitudinal axis of the cell 24 coincides with the axis of the light beam which the bulb 21 emits and which the photomultiplier 23 detects.

One of the considerable advantages of the analysis provided by the apparatus described is that the length of the layer of the solution in cell 24 through which the light beam passes is proportional to the volume of the solution. Accuracy ceases to be dependent upon the quantities of reagents in the solution, the only factors which are now concerned in accuracy being the quantity of samples and the diameter of the cell 24. Also, since the cover 25 is ejected, the distance between the light source 21 and the photomultiplier 23 when the same is in its lowered position is appreciably less than the total length of the analysis unit 17.

The reusable rotor 11 is removed from the apparatus for loading. Only the units 17 are changed for each analysis. The units 17, being closed units, can, with advantage, be pre-loaded in a series production operation with AFD reagents or appropriate liquids for the required analysis. All that the operator in charge of the analysis then has to do is to carry out the operations shown in FIGS. 6 and 7 and the operator can directly load the rotor 11 as shown in FIG. 4, whereafter he performs the other operations shown in FIGS. 8 to 11. Of course, the operator may have a number of rotors 11 available for a single analyzer, in which event he can prepare a number of rotors in advance without stopping the analyzer.

Another great advantage of the apparatus described is the system of temperature stabilization using a constantly renewed water bath around the cell 24 during analysis. The water temperature is under continuous supervision and the water is renewed for as long as the rotor 11 rotates.

The design of the charging and analysis unit 17 also has advantages. The unit 17 is of low cost and can therefore be discarded after use. Another advantage of the units 17 is the perforable cover 25 which acts as a storage cell before the sample and reagent are mixed together. Also, the cover 25 prevents any loss of solution when the rotor 11 is oscillated, as shown in FIG. 9. The advantage of the perforable cover 25 in connection with outside cleaning of the tip of the charging or loading needle has already been mentioned. Yet another advantage of the units 17 is that the cover 25 is readily removable once mixing and homogenization of the solution are finished. Also, since the end wall of the analysis cell 24 is recessed from the tube end and the same forms the window for the entry or exit of the light beam (depending on whether the light source is inside or outside the rotor), such end member is protected during handling from soiling and scratching likely to reduce its transparency and therefore impair the accuracy of measurement.

We claim:

1. A unit for containing a solution to be optically analysed and for mounting in a radial position on a centrifuging rotor, which unit comprises: a straight tubular cell for containing a first component of the solution and having one end open and the other end closed by an optically transparent wall which is substantially perpendicular to the longitudinal axis of the cell; a cover for closing the open end of said cell; and means releasably to secure the cover in a position closing the open end of the cell; the cover being formed with a recess for containing a second component of the solution and with at least one aperture connecting the said recess to the cell in the closed position, through which aperture the second component can flow into the cell during centrifuging.

2. A unit according to claim 1, wherein the cell and the cover are constituted by two straight tubular members nesting one in the other.

3. A unit according to claim 2, wherein the cell and the cover are of substantially the same volume as one another.

4. A unit according to claim 2, wherein the optically transparent wall is recessed relative to the end of the tubular member which constitutes the cell.

5. A unit according to claim 1, wherein the cover is made of a material which can be cold pierced by a metal point.

* * * * *